United States Patent [19]

Goodwin et al.

[11] 4,110,544
[45] Aug. 29, 1978

[54] PREPARATION OF CRESOLS

[75] Inventors: Thomas E. Goodwin, College Station, Tex.; Charles M. Starks, Ponca City, Okla.

[73] Assignee: Continental Oil Company, Ponca City, Okla.

[21] Appl. No.: 758,980

[22] Filed: Jan. 13, 1977

[51] Int. Cl.$^2$ .................. C07C 37/00; C07C 39/00
[52] U.S. Cl. .................................................. 568/805
[58] Field of Search .................. 260/621 D, 624 C; 252/463

[56] References Cited

U.S. PATENT DOCUMENTS

| | | | |
|---|---|---|---|
| 2,514,960 | 7/1950 | Luten | 260/621 D |
| 2,553,538 | 5/1951 | Arnold | 260/624 E |
| 3,091,646 | 5/1963 | Leston | 260/621 D |
| 3,502,595 | 3/1970 | Johnson et al. | 252/463 |
| 3,975,509 | 8/1976 | Royer et al. | 252/463 |

*Primary Examiner*—James O. Thomas, Jr.
*Assistant Examiner*—Werren B. Lone
*Attorney, Agent, or Firm*—Bayless E. Rutherford, Jr.

[57] ABSTRACT

A process for preparing cresols from di-hydrocarbyl-substituted cresols, wherein the hydrocarbyl groups contain from 3 to 7 carbon atoms, is disclosed. In the process the di-hydrocarbyl-substituted cresol is contacted with a catalyst (e.g. alumina) in the liquid phase at elevated temperatures and pressure. 4,6-di-t-butyl-m-cresol is a typical feedstock.

5 Claims, No Drawings

4,110,544

PREPARATION OF CRESOLS

BACKGROUND m-Cresol is a very useful chemical in that it is used to prepare many commercial products. For example, it is an intermediate in the preparation of 2,3,6-trimethylphenol, which is used to prepare vitamin E. In addition, it is an intermediate in the preparation of thymol, which is useful as a disinfectant and in the preparation of menthol.

o-Cresol and p-cresol are also useful chemicals in that many valuable products can be prepared from them.

While the present invention is directed primarily to the preparation of m-cresol it is also useful for the preparation of o-cresol and p-cresol.

PRIOR ART

The most pertinent reference is believed to be U.S. Pat. No. 3,091,646. In the background discussion on dealkylation of di-tertiary alkyl phenols the patent states that this can be done in vapor phase using alumina as the catalyst. The patent further states that vapor phase dealkylation is generally conducted at temperatures in the range of 350°–550° C. and thereby causes carbonaceous deposits to form on the surface of the catalyst.

We have found that when operating in the liquid phase at similar temperatures there is no carbonaceous deposit on the catalyst.

BRIEF SUMMARY OF THE INVENTION

Briefly stated, the present invention is directed to a process for preparing cresols from di-hydrocarbyl-substituted cresols, wherein the hydrocarbyl groups contain from 3 to 7 carbon atoms, wherein the process comprises contacting the di-hydrocarbyl-substituted cresols with an effective amount of a suitable catalyst in the liquid phase at elevated temperatures and pressures.

In a preferred embodiment the present invention is directed to a process for preparing m-cresol from di-t-alkylated cresols wherein the process comprises contacting the di-t-alkylated cresol with an effective amount of a suitable catalyst in the liquid phase at elevated temperatures and pressures.

The desired cresol product is recovered from the reaction mixture by means of fractional distillation.

DETAILED DESCRIPTION

Materials Used

The feedstocks used in our invention are di-hydrocarbyl-substituted cresols wherein the hydrocarbyl groups contain from 3 to 7 carbon atoms. While any of the cresol isomers are suitable the meta isomer is preferred. Also, more suitably the hydrocarbyl groups are alkyl groups (straight or branched-chain) containing 3 to 4 carbon atoms. A preferred material is di-t-butyl-m-cresol.

Specific examples of other suitable feedstocks include the following:
Di-(1-methylcyclohexyl)-m-cresol
Di-(1-methylcyclohexyl)-o-cresol
Di-(1-methylcyclohexyl)-p-cresol
Di-(1-methylcyclopentyl)-m-cresol
Di-(1-methylcyclopentyl)-o-cresol
Di-(1-methylcyclopentyl)-p-cresol
Di-t-amyl-m-cresol
Di-t-amyl-o-cresol
Di-t-amyl-p-cresol
Di-t-butyl-o-cresol
Di-t-butyl-p-cresol Suitable catalysts for use in our invention include activated alumina, synthetic silica-alumina, titania-alumina compositions containing from 0.01 to 5.0 percent by weight titania, titania and aluminum sulfate.

More suitable catalysts include synthetic silica-alumina and activated alumina.

Synthetic silica-alumina catalysts are well-known since they are frequently used in the refining of petroleum. Suitably, the synthetic silica-alumina catalysts contain from about 85 to about 90 weight percent silica (as $SiO_2$) and from about 10 to about 15 weight percent alumina (as $Al_2O_3$).

A preferred activated alumina for use in our process is one prepared by the hydrolysis of aluminum alkoxides. The preferred activated alumina has the following properties:

| | |
|---|---|
| Crystal Structure | α-alumina monohydrate |
| Surface Area, meters/gram | 230 – 300 |
| $Al_2O_3$, weight percent * | 70 – 75 |
| Loose bulk density, grams/liter | 650 – 720 |

*substantially all of the remainder is water.

A particularly suitable activated alumina is available from Conoco Chemicals Division of Continental Oil Company under the trademark "CATAPAL" SB.

The amount of catalyst is related to the liquid hourly space velocity (LHSV), which is defined as follows:

$$LHSV = \frac{\text{volume of liquid* per hour}}{\text{volume of catalyst}}$$

*in this instance the feedstock

A suitable range of LHSV is about 0.05 to about 50. A more suitable range of LHSV is about 1 to 10, with a range of 2 to 5 being preferred.

PROCESS CONDITIONS

An important feature of our process is conducting it under sufficient pressure that the reactants are in a liquid state.

A desirable feature of our process is that it can be operated on a continuous basis as well as a batch operation.

The suitable and preferred ranges for temperature, pressure and reaction time for conducting our process are set forth in the following table. It is to be understood that the process is operable under suitable conditions but that better results are obtained using the preferred conditions.

| | Suitable | Preferred |
|---|---|---|
| Temperature, ° C. | 200 – 600 | 250 – 400 |
| Pressure, atmospheres | 6 – 70 | 12 – 35 |
| Reaction time, min. | 1 – 1,000 | 5 – 75 |

The desired cresol product can be recovered from the reaction mixture by fractional distillation. Using di-t-butyl-m-cresol as a typical feedstock the fractions are as follows:
Main Cut 1 = isobutylene
Main Cut 2 = m-cresol Main Cut 3 = 2- and 4-t-butyl-3-methyl phenol and unreacted di-t-butyl-m-cresol (which can be recycled through the reactor).

In order to illustrate the nature of the present invention still more clearly the following examples will be given. It is to be understood, however, that the invention is not to be limited to the specific conditions or details set forth in these examples except insofar as such limitations are specified in the appended claims.

EXAMPLE 1

This example illustrates the preparation of m-cresol from 4,6-di-t-butyl-m-cresol. The catalyst was "CATAPAL" SB alumina.

The reaction was continuous using the following apparatus and procedure.

The reactor used was an electrically heated and controlled tube, ¼ inch in diameter and 10 inches long. It was fed through a Mill-Ray high pressure mini-pump from a feed-containing burette, and the pressure was controlled through a back pressure regulator. After exiting the back pressure regulator the product was passed through a water-cooled condenser. Liquid product was condensed and collected. Gaseous product was either passed out through a wet test meter where its volume was measured then through a sample container from which samples could be withdrawn for analysis, or it was passed through a condenser cooled with DRY-ICE and acetone to condense the low boiling components.

The reaction conditions were 370° C., 400 psig, and LHSV = 4.3. The isobutylene was collected in a dry ice-cooled trap.

The composition of the feedstock and of the remaining products is shown below.

| Component | Feedstock | Product (wt %) |
|---|---|---|
| m-cresol | — | 66.8 |
| monobutyl-m-cresols | 0.3 | 11.3 |
| di-butyl-m-cresol | 93.7 | — |
| unknowns | 5.9 | 21.9 |

EXAMPLE 2

This example illustrates the necessity of maintaining the feedstock in a liquid phase.

Di-t-butyl-m-cresol is passed over alumina (CATAPAL ® alumina, 1/16 inch extrudate) at a liquid hourly space velocity LHSV = 3.0 in the vapor phase. Maintenance of vapor phase is ensured by preheating the feed stream to 380° C. maintaining the catalyst bed at 390°–410° C. and keeping the pressure at atmospheric pressure. Debutylation of the feed occurs to yield isobutylene and m-cresol. However, the extent of conversion becomes lower and lower with time until after about 24–72 hours, so much deposition of carbonaceous material on the catalyst occurs that little m-cresol is produced.

EXAMPLE 3

This example is illustrative of the invention and comparative to Example 2.

In contrast to Example 2, when the reaction is conducted under sufficient back pressure (ca 300–500 psig) so as to maintain at least part of the reaction mixture in the liquid phase, but otherwise under the same conditions as above in the vapor phase, then deposition of material on the catalyst does not occur so rapidly, such that the reaction may be continued for several hundred hours without loss of activity.

Thus, having described the invention in detail, it will be understood by those skilled in the art that certain variations and modifications may be made without departing from the spirit and scope of the invention as defined herein and in the appended claims.

We claim:

1. A process for preparing m-cresols from di-t-butyl-m-cresol, said process comprising (1) contacting the di-t-butyl-m-cresol with an effective amount of a catalyst, which is selected from the group consisting of activated alumina and synthetic silica-alumina, in liquid phase at a temperature in the range of about 200° to about 600° C., a pressure in the range of about 6 to about 70 atmospheres, a reaction time of about 1 to about 75 minutes and the amount of catalyst, as feedstock to catalyst, is in a LHSV range of about 0.05 to about 50, and (b) recovering the m-cresols from the reaction mixture by fractional distillation.

2. The process of claim 1 wherein (a) the temperature is in the range of about 250° to about 400° C., (b) the pressure is in the range of about 12 to 35 atmospheres, and the reaction time is in the range of about 5 to about 75 minutes.

3. The process of claim 2 wherein the catalyst is a synthetic alumina which contains from about 85 to about 90 weight percent silica and from about 10 to about 15 weight percent alumina.

4. The process of claim 2 wherein the catalyst is activated alumina.

5. The process of claim 4 wherein the activated alumina has the following properties:

| Crystal Structure | α-alumina monohydrate |
|---|---|
| Surface area, meters/gram | 230 – 300 |
| Al$_2$O$_3$, wt. % | 70 – 75 |
| Loose bulk density, grams/liter | 650 – 720 |

* * * * *